(12) United States Patent
Xu et al.

(10) Patent No.: US 11,633,521 B2
(45) Date of Patent: Apr. 25, 2023

(54) BIOLOGIC BREAST IMPLANT

(71) Applicant: LifeCell Corporation, Madison, NJ (US)

(72) Inventors: Hui Xu, Plainsboro, NJ (US); Alexandra Pastino, Cherry Hill, NJ (US); Carrie Fang, Madison, NJ (US)

(73) Assignee: LifeCell Corporation, North Chicago, IL (US)

( * ) Notice: Subject to any disclaimer, the term of this patent is extended or adjusted under 35 U.S.C. 154(b) by 44 days.

(21) Appl. No.: 16/887,629

(22) Filed: May 29, 2020

(65) Prior Publication Data
US 2020/0376160 A1 Dec. 3, 2020

Related U.S. Application Data

(60) Provisional application No. 62/854,678, filed on May 30, 2019.

(51) Int. Cl.
*A61F 2/12* (2006.01)
*A61L 27/36* (2006.01)
*A61L 27/56* (2006.01)

(52) U.S. Cl.
CPC .......... *A61L 27/3633* (2013.01); *A61F 2/12* (2013.01); *A61L 27/3641* (2013.01); *A61L 27/3687* (2013.01); *A61L 27/3691* (2013.01); *A61L 27/56* (2013.01); *A61F 2230/0004* (2013.01); *A61F 2240/004* (2013.01)

(58) Field of Classification Search
CPC ..... A61F 2/12; A61L 27/3641; A61L 27/3633
USPC ........................................................ 623/7–8
See application file for complete search history.

(56) References Cited

U.S. PATENT DOCUMENTS

| | | |
|---|---|---|
| 4,233,969 A | 11/1980 | Lock et al. |
| 4,373,519 A | 2/1983 | Errede et al. |
| 4,569,348 A | 2/1986 | Hasslinger |
| 4,582,640 A | 4/1986 | Smestad et al. |
| 4,703,108 A | 10/1987 | Silver et al. |
| 4,902,508 A | 2/1990 | Badylak et al. |
| 4,950,483 A | 8/1990 | Ksander et al. |
| 4,969,912 A | 11/1990 | Kelman et al. |
| 5,024,841 A | 6/1991 | Chu et al. |
| 5,104,409 A | 4/1992 | Baker |
| 5,104,957 A | 4/1992 | Kelman et al. |
| 5,131,850 A | 7/1992 | Brockbank |
| 5,149,331 A | 9/1992 | Ferdman et al. |
| 5,160,313 A | 11/1992 | Carpenter et al. |

(Continued)

FOREIGN PATENT DOCUMENTS

| | | |
|---|---|---|
| EP | 1216718 A1 | 6/2002 |
| EP | 1683417 A1 | 7/2006 |

(Continued)

OTHER PUBLICATIONS

Ahn et al., The past, present, and future of xenotransplantation. Yonsei Med J. Dec. 31, 2004;45(6):1017-24.

(Continued)

*Primary Examiner* — Suzette J Gherbi
(74) *Attorney, Agent, or Firm* — McCarter & English, LLP

(57) ABSTRACT

The present disclosure provides tissue products produced from adipose tissues, as well as methods for producing such tissue products. The tissue products can include acellular tissue matrices for treatment of a breast.

19 Claims, 6 Drawing Sheets

(56) References Cited

U.S. PATENT DOCUMENTS

| | | |
|---|---|---|
| 5,231,169 A | 7/1993 | Constantz et al. |
| 5,254,133 A | 10/1993 | Seid |
| 5,263,971 A | 11/1993 | Hirshowitz et al. |
| 5,275,826 A | 1/1994 | Badylak et al. |
| 5,284,655 A | 2/1994 | Bogdansky et al. |
| 5,298,015 A | 3/1994 | Komatsuzaki et al. |
| 5,332,802 A | 7/1994 | Kelman et al. |
| 5,332,804 A | 7/1994 | Florkiewicz et al. |
| 5,336,616 A | 8/1994 | Livesey et al. |
| 5,364,756 A | 11/1994 | Livesey et al. |
| 5,437,651 A | 8/1995 | Todd et al. |
| 5,489,304 A | 2/1996 | Orgill et al. |
| 5,549,584 A | 8/1996 | Gross |
| 5,613,982 A | 3/1997 | Goldstein |
| 5,622,867 A | 4/1997 | Livesey et al. |
| 5,632,778 A | 5/1997 | Goldstein |
| 5,636,643 A | 6/1997 | Argenta et al. |
| 5,641,518 A | 6/1997 | Badylak et al. |
| 5,645,081 A | 7/1997 | Argenta et al. |
| 5,728,752 A | 3/1998 | Scopelianos et al. |
| 5,739,176 A | 4/1998 | Dunn et al. |
| 5,834,232 A | 11/1998 | Bishop et al. |
| 5,993,844 A | 11/1999 | Abraham et al. |
| 6,027,743 A | 2/2000 | Khouri et al. |
| 6,071,267 A | 6/2000 | Zamierowski |
| 6,096,347 A | 8/2000 | Geddes et al. |
| 6,135,116 A | 10/2000 | Vogel et al. |
| 6,179,872 B1 | 1/2001 | Bell et al. |
| 6,194,136 B1 | 2/2001 | Livesey et al. |
| 6,326,018 B1 | 12/2001 | Gertzman et al. |
| 6,345,623 B1 | 2/2002 | Heaton et al. |
| 6,371,992 B1 | 4/2002 | Tanagho et al. |
| 6,432,710 B1 | 8/2002 | Boss, Jr. et al. |
| 6,485,723 B1 | 11/2002 | Badylak et al. |
| 6,553,998 B2 | 4/2003 | Heaton et al. |
| 6,576,265 B1 | 6/2003 | Spievack |
| 6,599,318 B1 | 7/2003 | Gabbay |
| 6,613,278 B1 | 9/2003 | Mills et al. |
| 6,666,892 B2 | 12/2003 | Hiles et al. |
| 6,802,861 B1 | 10/2004 | Hamas |
| 6,814,079 B2 | 11/2004 | Heaton et al. |
| 6,840,960 B2 | 1/2005 | Bubb |
| 6,933,326 B1 | 8/2005 | Griffey et al. |
| 6,998,418 B1 | 2/2006 | Sung et al. |
| 7,070,584 B2 | 7/2006 | Johnson et al. |
| 7,153,518 B2 | 12/2006 | Wironen et al. |
| 7,198,046 B1 | 4/2007 | Argenta et al. |
| 7,358,284 B2 | 4/2008 | Griffey et al. |
| 7,425,322 B2 | 9/2008 | Cohn et al. |
| 7,498,040 B2 | 3/2009 | Masinaei et al. |
| 7,498,041 B2 | 3/2009 | Masinaei et al. |
| 7,700,819 B2 | 4/2010 | Ambrosio et al. |
| 7,763,769 B2 | 7/2010 | Johnson et al. |
| 7,799,767 B2 | 9/2010 | Lamberti et al. |
| 7,838,021 B2 | 11/2010 | Lafont et al. |
| 8,067,149 B2 | 11/2011 | Livesey et al. |
| 8,110,216 B2 | 2/2012 | Ambrosio et al. |
| 8,152,783 B2 | 4/2012 | Swain |
| 8,163,974 B2 | 4/2012 | Ambrosio et al. |
| 8,197,551 B2 | 6/2012 | Swain et al. |
| 8,197,806 B2 | 6/2012 | Girouard et al. |
| 8,257,372 B2 | 9/2012 | Swain et al. |
| 8,267,918 B2 | 9/2012 | Johnson et al. |
| 8,324,449 B2 | 12/2012 | McQuillan et al. |
| 9,375,513 B2 | 6/2016 | Sun et al. |
| 9,532,863 B2 | 1/2017 | Hayzlett |
| 9,782,436 B2 | 10/2017 | Sun |
| 10,058,416 B2 | 8/2018 | Corbitt, Jr. |
| 10,092,392 B2 | 10/2018 | Nieto et al. |
| 10,314,861 B2 | 6/2019 | Sun |
| 2002/0103542 A1 | 8/2002 | Bilbo |
| 2002/0120185 A1 | 8/2002 | Johnson |
| 2002/0193448 A1 | 12/2002 | Wallace et al. |
| 2003/0035843 A1 | 2/2003 | Livesey et al. |
| 2003/0039678 A1 | 2/2003 | Stone et al. |
| 2003/0104026 A1 | 6/2003 | Wironen et al. |
| 2003/0143207 A1 | 7/2003 | Livesey et al. |
| 2003/0147935 A1 | 8/2003 | Binette et al. |
| 2003/0225347 A1 | 12/2003 | Argenta et al. |
| 2004/0037735 A1 | 2/2004 | DePaula et al. |
| 2004/0078077 A1 | 4/2004 | Binette et al. |
| 2004/0162613 A1* | 8/2004 | Roballey ................... A61F 2/12 623/8 |
| 2005/0028228 A1 | 2/2005 | McQuillan et al. |
| 2005/0043819 A1 | 2/2005 | Schmidt et al. |
| 2005/0125077 A1 | 6/2005 | Harmon et al. |
| 2005/0159822 A1 | 7/2005 | Griffey et al. |
| 2005/0260176 A1 | 11/2005 | Ayares et al. |
| 2006/0058892 A1 | 3/2006 | Lesh et al. |
| 2006/0073592 A1 | 4/2006 | Sun et al. |
| 2006/0127375 A1 | 6/2006 | Livesey et al. |
| 2006/0153816 A1 | 7/2006 | Brown et al. |
| 2006/0210960 A1 | 9/2006 | Livesey et al. |
| 2007/0004961 A1 | 1/2007 | Case et al. |
| 2007/0071729 A1 | 3/2007 | Bernstein |
| 2007/0078522 A2 | 4/2007 | Griffey et al. |
| 2007/0104759 A1 | 5/2007 | Dunn et al. |
| 2007/0219471 A1 | 9/2007 | Johnson et al. |
| 2007/0248575 A1 | 10/2007 | Connor et al. |
| 2008/0027542 A1 | 1/2008 | McQuillan et al. |
| 2008/0027562 A1 | 1/2008 | Fujisato et al. |
| 2008/0114277 A1 | 5/2008 | Ambrosio et al. |
| 2008/0279824 A1 | 11/2008 | Matheny et al. |
| 2008/0281418 A1 | 11/2008 | Firestone |
| 2008/0281419 A1 | 11/2008 | Matheny et al. |
| 2009/0024224 A1 | 1/2009 | Chen et al. |
| 2009/0035289 A1 | 2/2009 | Wagner et al. |
| 2009/0157017 A1 | 6/2009 | Ambrosio |
| 2009/0198167 A1 | 8/2009 | Ambrosio |
| 2009/0220579 A1 | 9/2009 | Hassingboe et al. |
| 2009/0287181 A1 | 11/2009 | Kagan |
| 2009/0306790 A1 | 12/2009 | Sun |
| 2009/0326515 A1 | 12/2009 | Kagan |
| 2010/0021961 A1 | 1/2010 | Fujisato et al. |
| 2010/0040687 A1 | 2/2010 | Pedrozo et al. |
| 2010/0058952 A1 | 3/2010 | Yang et al. |
| 2010/0168689 A1 | 7/2010 | Swain et al. |
| 2010/0168720 A1 | 7/2010 | Swain et al. |
| 2010/0168870 A1 | 7/2010 | Swain et al. |
| 2010/0179515 A1 | 7/2010 | Swain et al. |
| 2010/0209408 A1 | 8/2010 | Stephen A. et al. |
| 2010/0272782 A1 | 10/2010 | Owens et al. |
| 2011/0020271 A1 | 1/2011 | Niklason et al. |
| 2011/0022171 A1 | 1/2011 | Richter et al. |
| 2011/0184357 A1 | 7/2011 | Robinson et al. |
| 2011/0251566 A1 | 10/2011 | Zimnitsky et al. |
| 2012/0010728 A1 | 1/2012 | Sun et al. |
| 2012/0040013 A1 | 2/2012 | Owens et al. |
| 2012/0189588 A1 | 7/2012 | Nahas et al. |
| 2012/0310367 A1 | 12/2012 | Connor |
| 2013/0053960 A1 | 2/2013 | Park et al. |
| 2013/0121970 A1 | 5/2013 | Owens et al. |
| 2013/0122068 A1 | 5/2013 | Fermanian et al. |
| 2013/0158676 A1 | 6/2013 | Hayzlett et al. |
| 2013/0261745 A1 | 10/2013 | Van Epps |
| 2013/0280223 A1 | 10/2013 | Owens et al. |
| 2013/0280801 A1 | 10/2013 | Sun |
| 2015/0037436 A1 | 2/2015 | Huang et al. |
| 2015/0150675 A1 | 6/2015 | Mora et al. |
| 2015/0351900 A1 | 12/2015 | Glicksman |
| 2016/0235892 A1 | 8/2016 | Detamore et al. |
| 2016/0271295 A1 | 9/2016 | Sun et al. |
| 2017/0224869 A1* | 8/2017 | Shah ................... A61L 27/3691 |
| 2018/0353644 A1 | 12/2018 | Sun et al. |
| 2019/0076582 A1* | 3/2019 | Connor ................... A61L 27/58 |
| 2019/0111183 A1* | 4/2019 | Xu ........................ A61L 27/56 |
| 2019/0117833 A1 | 4/2019 | Xu et al. |
| 2019/0262394 A1 | 8/2019 | Sun |
| 2020/0000855 A1* | 1/2020 | Xu ........................ A61L 27/48 |
| 2020/0114091 A1 | 4/2020 | Xu et al. |
| 2021/0038767 A1* | 2/2021 | Xu ........................ A61L 27/48 |

(56) References Cited

U.S. PATENT DOCUMENTS

| | | | | |
|---|---|---|---|---|
| 2021/0244860 A1* | 8/2021 | Williams | ............... | A61B 17/72 |
| 2021/0353831 A1* | 11/2021 | Seidner H. | ............ | A61L 27/20 |

FOREIGN PATENT DOCUMENTS

| | | |
|---|---|---|
| EP | 1433423 B1 | 12/2008 |
| WO | WO-1990/00060 A1 | 1/1990 |
| WO | WO-1998/44809 A1 | 10/1998 |
| WO | WO-1999/32049 A1 | 7/1999 |
| WO | WO-1999/65470 A1 | 12/1999 |
| WO | WO-2000/016822 A1 | 3/2000 |
| WO | WO-2000/047114 A1 | 8/2000 |
| WO | WO-2002/40630 A2 | 5/2002 |
| WO | WO-2003/017826 A2 | 3/2003 |
| WO | WO-2005/120597 A1 | 12/2005 |
| WO | WO-2007/043513 A1 | 4/2007 |
| WO | WO-2008/134305 A2 | 11/2008 |
| WO | WO-2011/019822 A2 | 2/2011 |
| WO | WO-2011/046806 A1 | 4/2011 |
| WO | WO-2017/029633 A1 | 2/2017 |

OTHER PUBLICATIONS

Allman et al., Xenogeneic extracellular matrix grafts elicit a TH2-restricted immune response. Transplantation. Jun. 15, 2001;71(11):1631-40.

B-Bridge International, Inc., Type 1 Collagenase Assay Kit. Catalog # AK07. www.b-bridge.com. 4 pages (2009).

Badylak et al., Extracellular matrix as a biological scaffold material: Structure and function. Acta Biomater. Jan. 2009;5(1):1-13.

BC BioLibrary, Sectioning of OCT Embedded Tissue. Retrieved online at: http://www.bcbiolibrary.icapture.ubc.ca/pathologists-researchers/docs/BL.LAB.GN.002.01%20Sectioning%20of%20OCT%20Embedded%20Tissue.pdf. 4 pages, (2008).

Chaplin et al., Use of an acellular dermal allograft for dural replacement: an experimental study. Neurosurgery. Aug. 1999;45(2):320-7.

Chariker et al., Effective management of incisional and cutaneous fistulae with closed suction wound drainage. Contemporary Surgery. Jun. 1989;34:59-63.

Chen et al., Acellular collagen matrix as a possible "off the shelf" biomaterial for urethral repair. Urology. Sep. 1999;54(3):407-10.

Choi et al., Decellularized extracellular matrix derived from human adipose tissue as a potential scaffold for allograft tissue engineering. J Biomed Mater Res A. Jun. 1, 2011;97(3):292-9.

Choi et al., Fabrication of porous extracellular matrix scaffolds from human adipose tissue. Tissue Eng Part C Methods. Jun. 2010;16(3):387-96.

Costantino et al., Human dural replacement with acellular dermis: clinical results and a review of the literature. Head Neck. Dec. 2000;22(8):765-71.

Dagalakis et al., Design of an artificial skin. Part III. Control of pore structure. J Biomed Mater Res. Jul. 1980;14(4):511-28.

Dattilo et al., Medical Textiles: Application of an Absorbable Barbed Bi-directional Surgical Suture. Journal of Textile and Apparel, Technology and Management. 2002 Spring;2(2):1-5.

Fowler et al., Root coverage with an acellular dermal allograft: a three-month case report. J Contemp Dent Pract. Aug. 15, 2000;1(3):47-59.

Galili et al., Interaction between human natural anti-alpha-galactosyl immunoglobulin G and bacteria of the human flora. Infect Immun. Jul. 1988;56(7):1730-7.

Galili et al., Man, apes, and Old World monkeys differ from other mammals in the expression of alpha-galactosyl epitopes on nucleated cells. J Biol Chem. Nov. 25, 1988;263(33):17755-62.

Galili, Interaction of the natural anti-Gal antibody with alpha-galactosyl epitopes: a major obstacle for xenotransplantation in humans. Immunol Today. Oct. 1993;14(10):480-2.

Lu et al., Novel porous aortic elastin and collagen scaffolds for tissue engineering. Biomaterials. Oct. 2004;25(22):5227-37.

Marzaro et al., Autologous satellite cell seeding improves in vivo biocompatibility of homologous muscle acellular matrix implants. Int J Mol Med. Aug. 2002;10(2):177-82.

O'Brien et al., The effect of pore size on cell adhesion in collagen-GAG scaffolds. Biomaterials. Feb. 2005;26(4):433-41.

Wei et al., Construction of varying porous structures in acellular bovine pericardia as a tissue-engineering extracellular matrix. Biomaterials. May 2005;26(14):1905-13.

Wu et al., An Injectable Adipose Matrix for Soft Tissue Reconstruction. Plastic and Reconstructive Surgery Advance Online Article. DOI: 10.1097/PRS.0b013e31824ec3dc. 33 pages, (2012).

Wu et al., Preparation of collagen-based materials for wound dressing. Chin Med J (Engl). Mar. 2003;116(3):419-23.

Xu et al., A porcine-derived acellular dermal scaffold that supports soft tissue regeneration: removal of terminal galactose-alpha-(1,3)-galactose and retention of matrix structure. Tissue Eng Part A. Jul. 2009;15(7):1807-19.

Yang et al., A cartilage ECM-derived 3-D porous acellular matrix scaffold for in vivo cartilage tissue engineering with PKH26-labeled chondrogenic bone marrow-derived mesenchymal stem cells. Biomaterials. May 2008;29(15):2378-87.

U.S. Appl. No. 13/483,674, filed May 30, 2012, 2012-0310367, Published.

U.S. Appl. No. 16/189,468, filed Nov. 13, 2018, 2019-0076582, Published.

U.S. Appl. No. 15/416,583, filed Jan. 26, 2017, 2017-0224869, Published.

U.S. Appl. No. 16/164,177, filed Oct. 18, 2018, 2019-0111183, Published.

U.S. Appl. No. 16/502,640, filed Jul. 3, 2019, 2020-0000855, Published.

* cited by examiner

BIOLOGIC BREAST IMPLANT

This application claims priority under 35 U.S.C. § 119 to U.S. Provisional Application No. 62/854,678, filed May 30, 2019, the entire contents of which is incorporated herein by reference.

The present disclosure relates to tissue products, and more particularly, to extracellular tissue matrices made from adipose tissue.

Various tissue-derived products are used to regenerate, repair, or otherwise treat diseased or damaged tissues and organs. Such products can include tissue grafts and/or processed tissues (e.g., acellular tissue matrices from skin, intestine, or other tissues, with or without cell seeding). Such products generally have properties determined by the tissue source (i.e., tissue type and animal from which it originated) and the processing parameters used to produce the tissue products. Since tissue products are often used for surgical applications and/or tissue replacement or augmentation, the products should support tissue growth and regeneration, as desired for the selected implantation site. The present disclosure provides adipose tissue products that can allow improved tissue growth and regeneration for various applications, such as breast implants.

According to certain embodiments, methods for producing tissue products are provided. The methods can include selecting an adipose tissue; mechanically processing the adipose tissue to reduce the tissue size; treating the mechanically processed tissue to remove substantially all cellular material from the tissue; suspending the tissue in a liquid to form a suspension; and drying the suspension in the mold to form a porous sponge.

In various embodiments, the adipose tissue is processed to control certain mechanical properties. For example, the processed tissue can be cross-linked to produce a stable three-dimensional structure. Additionally, or alternatively, the percent solid content of the sponge or suspension can be controlled, as discussed in further detail below.

Also provided herein are tissue products made by the disclosed processes.

In some embodiments, the tissue products include a decellularized adipose extracellular tissue matrix, wherein the tissue matrix has been formed into a predetermined three-dimensional shape, and wherein the tissue matrix is partially cross-linked to maintain the three-dimensional shape.

Also provided herein is a tissue product comprising a breast implant. The implant can comprise an adipose tissue matrix formed with a desired set of mechanical properties controlled by cross-linking and/or percent solids.

Further provided herein are methods of treatment comprising the steps of selecting a tissue site and implanting the tissue products disclosed herein into the tissue site. The methods can include implanting the treatment device in or proximate a wound or surgical site and securing at least a portion of the treatment device to tissue in or near the treatment site. The tissue product may be implanted behind the tissue site to bolster, reposition, or project the native tissue outward.

DESCRIPTION OF CERTAIN EXEMPLARY EMBODIMENTS

Figure 1:
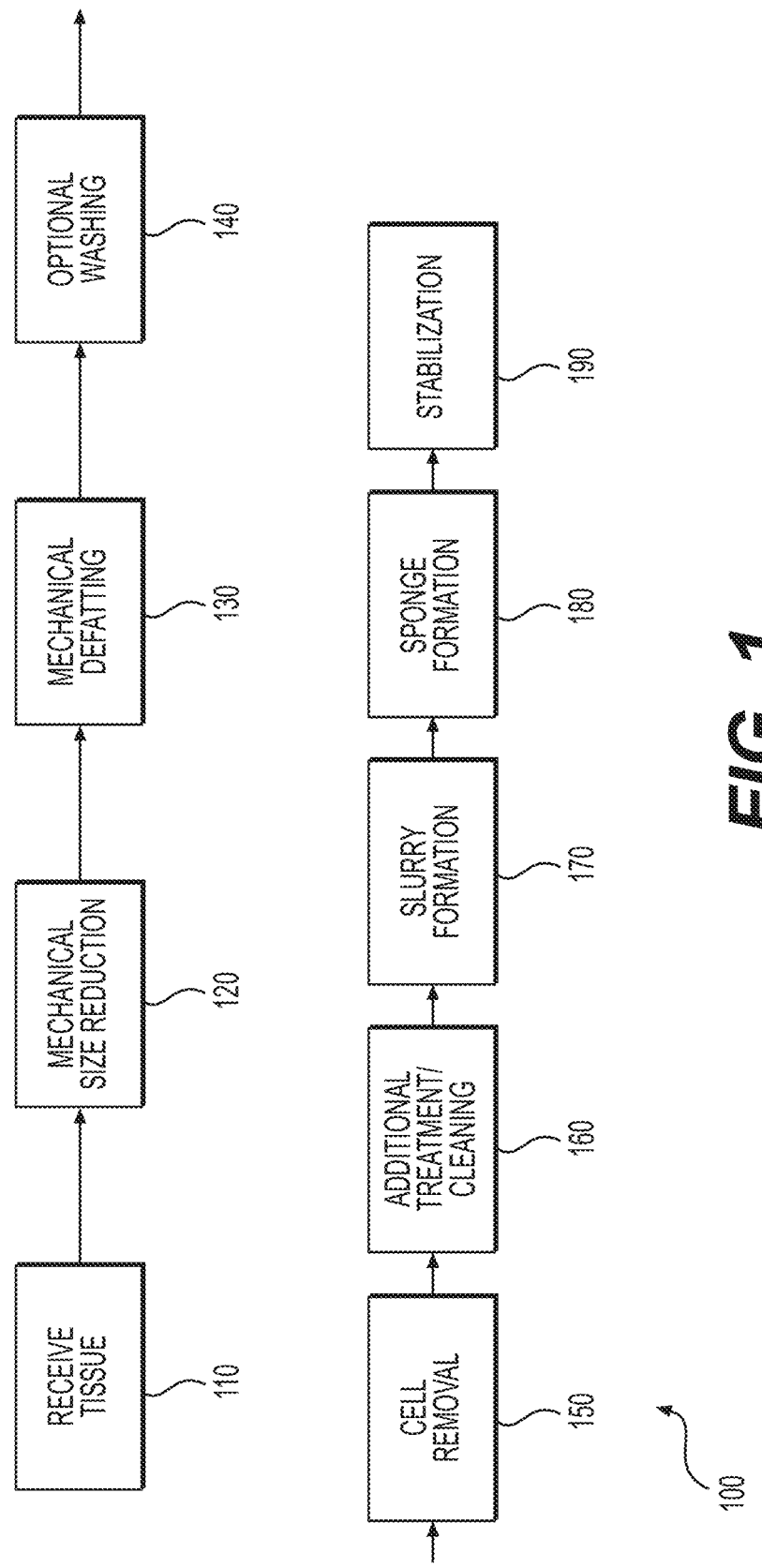
FIG. 1 is a flow chart outlining a process for producing an adipose tissue matrix sponge, according to certain embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein "tissue product" will refer to any human or animal tissue that contains an extracellular matrix protein. "Tissue products" may include acellular or partially decellularized tissue matrices, as well as decellularized tissue matrices that have been repopulated with exogenous cells.

As used herein, the term "acellular tissue matrix" refers to an extracellular matrix derived from human or animal tissue, wherein the matrix retains a substantial amount of natural collagen, other proteins, proteoglycans, and glycoproteins needed to serve as a scaffold to support tissue regeneration. "Acellular tissue matrices" are different from the purified collagen materials, such as acid-extracted purified collagen, which are substantially void of other matrix proteins and do not retain the natural micro-structural features of tissue matrix due to the purification processes. Although referred to as "acellular tissue matrices," it will be appreciated that such tissue matrices may be combined with exogenous cells, including, for example, stem cells, or cells from a patient in whom the "acellular tissue matrices" may be implanted. A "decellularized adipose tissue matrix" will be understood to refer to an adipose-based tissue from which all cells have been removed to produce adipose extracellular matrix. "Decellularized adipose tissue matrix" can include intact matrix or matrix that has been further processed as discussed herein, including mechanical processing, formation of a sponge, and/or further processing to produce particulate matrix.

"Acellular" or "decellularized" tissue matrices will be understood to refer to tissue matrices in which no cells are visible using light microscopy.

Various human and animal tissues may be used to produce products for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products may include, for example, acellular tissue matrices, tissue allografts or xenografts, and/or reconstituted tissues (i.e., at least partially decellularized tissues that have been seeded with cells to produce viable materials).

A variety of tissue products have been produced for treating soft and hard tissues. For example, ALLODERM® and STRATTICE® (LIFECELL CORPORATION, BRANCHBURG, N.J.) are two dermal acellular tissue matrices made from human and porcine dermis, respectively. Although such materials are very useful for treating certain types of conditions, materials having different biological and mechanical properties may be desirable for certain applications. For example, ALLODERM® and STRATTICE® have been used to assist in the treatment of structural defects and/or to provide support to tissues (e.g., for abdominal walls or in breast reconstruction), and their strength and biological properties make them well suited for such uses. However, such materials may not be ideal for regeneration, repair, replacement, and/or augmentation of adipose-containing tissues, when the desired result is production of adipose tissue with viable adipocytes. Accordingly, the present disclosure provides tissue products that are useful for the treatment of tissue defects/imperfections involving adipose-containing tissues. The present disclosure also provides methods for producing such tissue products.

The tissue products may include adipose tissues that have been processed to remove at least some of the cellular components. In some cases, all, or substantially all cellular materials are removed, thereby leaving adipose extracellular matrix proteins. In addition, the products may be processed to remove some or all of the extracellular and/or intracellular lipids. In some cases, however, complete removal of extracellular and/or intracellular lipids can be damaging to the architecture and functions of the adipose matrix. For example, adipose tissues that are chemically or enzymatically treated for an extended period of time may have denatured or otherwise damaged collagen, or may be depleted of proteins needed for adipose regeneration. Accordingly, in some cases, the product contains a certain level of residual lipids. The remaining lipid content can be, for example, about 5%, 6%, 7%, 8%, 9%, or 10% by weight of the product. As described further below, the extracellular matrix proteins may be further treated to produce a three-dimensional porous, or sponge-like material, and the porous or sponge-like material may be further processed to produce an injectable product.

As noted, the tissue products of the present disclosure are formed from adipose tissues. The adipose tissues may be derived from human or animal sources. For example, human adipose tissue may be obtained from cadavers. In addition, human adipose tissue could be obtained from live donors (e.g., with autologous tissue). Adipose tissue may also be obtained from animals such as pigs, monkeys, or other sources. If animal sources are used, the tissues may be further treated to remove antigenic components such as 1,3-alpha-galactose moieties, which are present in pigs and other mammals, but not humans or primates. See Xu, Hui, et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009), which is hereby incorporated by reference in its entirety. In addition, the adipose tissue may be obtained from animals that have been genetically modified to remove antigenic moieties.

An exemplary process for producing the tissue products of the present disclosure is illustrated in FIG. 1. FIG. 1 provides a flow chart illustrating the basic steps that may be used to produce a suitable adipose tissue sponge, which can then be further processed to produce injectable or implantable particulate. As shown, the process may include a number of steps, but it will be understood that additional or alternative steps may be added or substituted depending on the particular tissue being used, desired application, or other factors.

As shown, the process 100 may begin generally at Step 110, wherein tissue is received. The tissue may include a variety of adipose tissue types, including, for example, human or animal adipose tissue. Suitable tissue sources may include allograft, autograft, or xenograft tissues. When xenografts are used, the tissue may include adipose from animals including porcine, cow, dog, cat, domestic or wild sources, and/or any other suitable mammalian or non-mammalian adipose source.

The tissue may be harvested from animal sources using any desirable technique, but may be generally obtained using, if possible, aseptic or sterile techniques. The tissue may be stored in cold or frozen conditions or may be immediately processed to prevent any undesirable changes due to prolonged storage.

After receiving the tissue, the tissue may initially be subject to mechanical size reduction at Step 120 and/or mechanical defatting at Step 130. Mechanical size reduction may include gross or large cutting of tissue using manual blades or any other suitable grinding process.

Mechanical defatting at Step 130 may be important in the production of tissue. Specifically, to assist in lipid removal, the adipose may be subject to a variety of mechanical processing conditions. For example, the mechanical processing may include grinding, blending, chopping, grating, or otherwise processing the tissue. The mechanical processing may be performed under conditions that allow for a certain degree of heating, which may assist in liberating or removing lipids. For example, the mechanical processing may be performed under conditions that may allow the adipose tissue to heat up to 122° F. (50° C.), or between 42-45° C. for porcine adipose or somewhat lower temperatures for human adipose. The application of external heat may be insufficient to release the lipids; therefore, heat generated during mechanical disruption may be preferred to assist in lipid removal. In some examples, heating during mechanical processing may be a pulse in temperature rise and may be short in duration. This heat pulse may cause liquification of lipid released from broken fat cells by mechanical disruption, which may then cause efficient phase separation for bulk lipid removal. In an example, when processing a porcine adipose tissue, the temperature reached during this process is above 100° F. and may not exceed 122° F. (50° C.). The range of temperature reached can be adjusted according to the origin of the adipose tissue. For example, the temperature can be further lowered to about 80° F., 90° F., 100° F., 110° F., or 120° F. when processing less-saturated tissues, e.g., primate tissues. Alternatively, the process may be selected to ensure the adipose reaches a minimum temperature such as 80° F., 90° F., 100° F., 110° F., or 120° F.

In some cases, the mechanical defatting may be performed by mechanically processing the tissue with the addition of little or no washing fluids. For example, the tissue may be mechanically processed by grinding or blending without the use of solvents. Alternatively, when grinding the tissue requires moisture, for example to increase flowability or decrease viscosity, water may be used, including pure water or saline or other buffers including saline or phosphate buffered saline. In some examples, the tissue may be processed by adding a certain quantity of solvent that is biocompatible, such as saline (e.g., normal saline, phosphate buffered saline, or solutions including salts and/or detergents). Other solutions that facilitate cell lysis may also be appropriate, including salts and/or detergents.

After mechanical processing and lipid removal, the adipose may be washed at Step 140. For example, the tissue may be washed with one or more rinses with various biocompatible buffers. For example, suitable wash solutions may include saline, phosphate buffered saline, or other suitable biocompatible materials or physiological solutions. In an example, water may be used as a rinsing agent to further break the cells, after which phosphate buffered saline, or any other suitable saline solution, may be introduced to allow the matrix proteins to return to biocompatible buffers.

The washing may be performed along with centrifugation or other processes to separate lipids from the tissue. For example, in some embodiments, the material is diluted with water or another solvent. The diluted material is then centrifuged, and free lipids will flow to the top, while the extracellular matrix proteins are deposited as a pellet. The protein pellet may then be resuspended, and the washing and centrifugation may be repeated until a sufficient amount of the lipids are removed.

After any washing, the adipose may be treated to remove some or all cells from the adipose tissue as indicated at Step 150. The cell removal process may include a number of suitable processes. For example, suitable methods for removing cells from the adipose tissue may include treatment with detergents such as deoxycholic acid, polyethylene glycols, or other detergents at concentrations and times sufficient to disrupt cells and/or remove cellular components.

After cell removal, additional processing and/or washing steps may be incorporated, depending on the tissue used or ultimate structure desired, as indicated at Step 160. For example, additional washing or treatment may be performed to remove antigenic materials such as alpha-1,3-galactose moieties, which may be present on non-primate animal tissues. In addition, during, before, and/or after the washing steps, additional solutions or reagents may be used to process the material. For example, enzymes, detergents, and/or other agents may be used in one or more steps to further remove cellular materials or lipids, remove antigenic materials, and/or reduce the bacteria or other bioburden of the material. For example, one or more washing steps may be included using detergents, such as sodium dodecyl sulfate or Triton to assist in cell and lipid removal. In addition, enzymes such as lipases, DNAses, RNAses, alpha-galactosidase, or other enzymes may be used to ensure destruction of nuclear materials, antigens from xenogenic sources, residual cellular components and/or viruses. Further, acidic solutions and/or peroxides may be used to help further remove cellular materials and destroy bacteria and/or viruses, or other potentially infectious agents.

After removal of lipids and cellular components, the material may then be formed into a porous or sponge-like material. Generally, the extracellular matrix is first resuspended in an aqueous solvent to form a slurry-like material as indicated at Step 170. A sufficient amount of solvent is used to allow the material to form a liquid mass that may be poured into a mold having the size and shape of the desired tissue product. The amount of water or solvent added may be varied based on the desired porosity of the final material. In some cases, the slurry-like material may have a solid concentration of about 2% to about 10% by weight, preferably about 2% to about 5%. In some cases, the resuspended extracellular matrix may be mechanically treated by grinding, cutting, blending or other processes one or more additional times, and the treated material may be centrifuged and resuspended one or more times to further remove cellular material or lipids (if needed) and/or to control the viscosity of the extracellular matrix.

Once any additional washing and grinding steps are complete, the resuspended material is placed in a container or mold to form the porous, sponge-like product, as indicated at Step 180. Generally, the porous or sponge-like material is formed by drying the material to leave a three-dimensional matrix with a porous structure. In some embodiments, the material is freeze-dried. Freeze-drying may allow production of a three-dimensional structure that generally conforms to the shape of the mold, as shown in FIG. 3. The specific freeze drying protocol may be varied based on the solvent used, sample size, and/or to optimize processing time. One suitable freeze-drying process may include cooling the material for a period of time; holding the samples at a constant temperature of a period of time and further cooling down the sample to insure complete freezing; applying a vacuum; raising the temperature and holding the temperature for a period of time; raising the temperature again and holding the temperature for a period time. The freeze-dried samples may then be removed from the freeze-dryer and packaged in foil pouches under nitrogen.

After formation of a solid or sponge, the material may optionally be stabilized, as indicated at Step 190. In some cases, the stabilization may include additional processes such as cross-linking, treatment with dehydrothermal (DHT) processes, or other suitable stabilization methods. For example, generally, a mechanically processed tissue, when formed into a porous matrix, may form a more putty- or paste-like material when it is implanted in a body, becomes wet, or is placed in a solution. Therefore, the desired shape and size may be lost. In addition, the porous structure, which may be important for supporting cell attachment, tissue growth, vascular formation, and tissue regeneration, may be lost. Accordingly, the material may be further processed to stabilize the size, shape, and structure of the material.

In some embodiments, the material is cross-linked for stabilization. In some embodiments, the material is cross-linked after freeze drying. However, the material could also be cross-linked before or during the freeze-drying process. Cross-linking may be performed in a variety of ways. In one embodiment, cross-linking is accomplished by contacting the material with a cross-linking agent such as glutaraldehyde, genepin, carbodiimides (e.g., 1-ethyl-3-(3-dimethylaminopropyl) carbodiimide hydrochloride (EDC)), and diisocyantes.

In addition, cross-linking may be performed by heating the material in a vacuum. For example, in some embodiments, the material may be heated to between 70° C. to 120° C., or between 80° C. and 110° C., or to about 100° C., or any values between the specified ranges in a reduced pressure or vacuum. In addition, other cross-linking processes, or combination of processes, may be used to produce any of the disclosed products, including ultraviolet irradiation, gamma irradiation, and/or electron beam (e-beam) irradiation. In addition, a vacuum is not needed but may reduce cross-linking time. Further, lower or higher temperatures could be used as long as melting of the matrix proteins does not occur and/or sufficient time is provided for cross-linking.

In various embodiments, the cross-linking process may be controlled to produce a tissue product with desired mechanical, biological, and/or structural features. For example, cross-linking may influence the overall strength of the material, and the process may be controlled to produce a desired strength. In addition, the amount of cross-linking may affect the ability of the product to maintain a desired shape and structure (e.g., porosity) when implanted. Accordingly, the amount of cross-linking may be selected to produce a stable three-dimensional shape when implanted in a body, when contacted with an aqueous environment, and/or when compressed (e.g., by surrounding tissues or materials).

Excessive cross-linking may change the extracellular matrix materials. For example, excessive cross-linking may damage collagen or other extracellular matrix proteins. The damaged proteins may not support tissue regeneration when the tissue products are placed in an adipose tissue site or other anatomic location. In addition, excessive cross-linking may cause the material to be brittle or weak. Accordingly, the amount of cross-linking may be controlled to produce a desired level of stability, while maintaining desired biological, mechanical, and/or structural features.

Exemplary cross-linking processes may include contacting a freeze-dried material, produced as discussed above, with glutaraldehyde or EDC. For example, a 0.1% glutaraldehyde solution may be used, and the tissue may be submerged in the solution for about for 18 hours followed by extensive rinsing in water to remove the solution. Alternatively, or in combination, a dehydrothermal (DHT) process may be used. For example, one exemplary dehydrothermal process includes treating the material at 100° C. and ~20 inches of Hg for 18 hours, followed by submersion in water. The final cross-linked tissue products may be stored in a film pouch.

Figure 2:
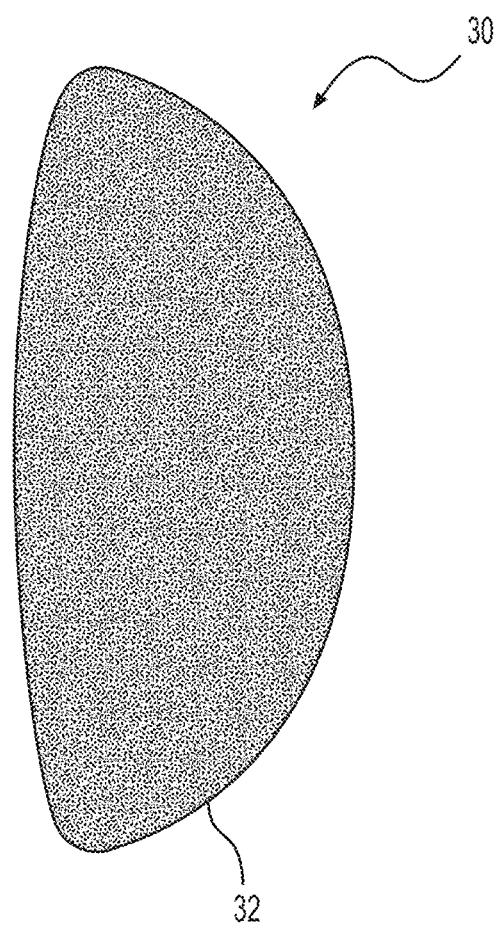
FIG. 2 is a side view of a biologic breast implant having a layered construct, according to certain embodiments.
Figure 3A:
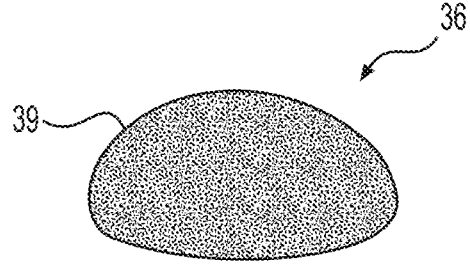
FIG. 3A is a perspective view of a configuration for a breast implant, having a layered construct, according to certain embodiments.
Figure 3B:
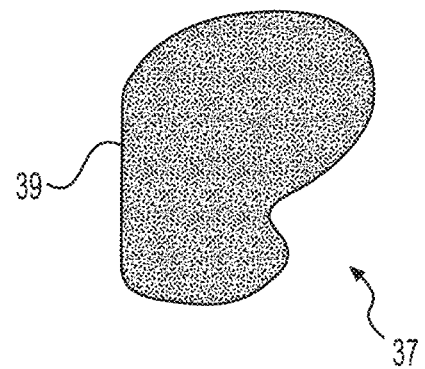
FIG. 3B is a perspective view of another configuration for a breast implant, having a layered construct, according to certain embodiments.
Figure 3C:
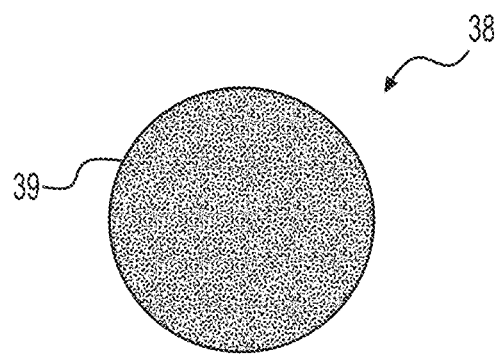
FIG. 3C is a perspective view of another configuration for a breast implant, having a layered construct, according to certain embodiments.

The devices produced using the above-discussed methods can have a variety of configurations. For example, FIG. 2 is a side view of a biologic breast implant 30 formed of an adipose tissue matrix. The implant can include a variety of suitable breast implant shapes, contours, or projections. Further, it should be appreciated that a variety of shapes can be used, including rounded, irregular, concentric spheroid, or concentric irregular 3-D shapes, or custom-formed implants. For example, FIGS. 3A-3C illustrate exemplary shapes for implants produced using the disclosed methods, including tear-drop implants 36 (FIG. 3A), irregular implants 37 (FIG. 3B), and/or spherical implants 38 (FIG. 3C), each formed of layers 39.

The device 30, 36-38 can have a variety of sizes. But as noted above, the methods provided herein can provide advantages by allowing production of adipose implants having large sizes that can match those of conventional breast implants or tissue expanders. For example, using the layering methods discussed herein, implants having at least one dimension of 5 cm or greater can be produced. In other cases, the devices have a dimension of at least 6 cm, at least 7 cm, at least 8 cm, at least 10 cm, or larger.

Figure 4:
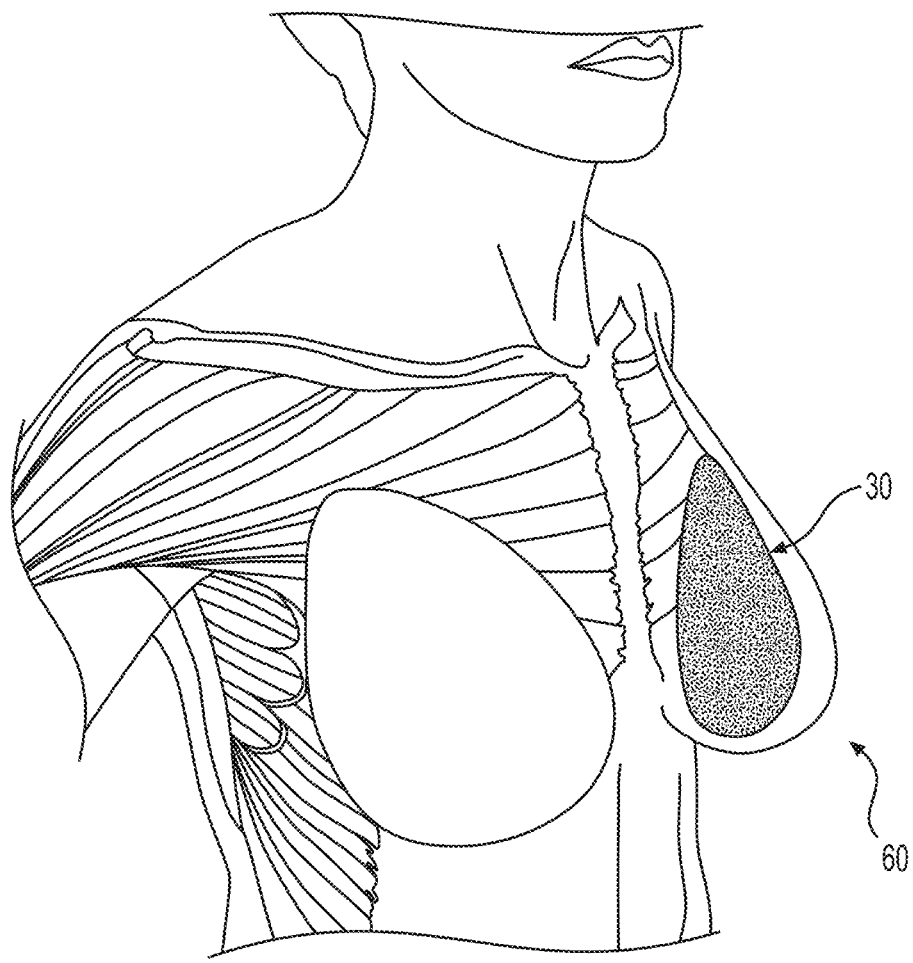
FIG. 4 illustrates implantation of a system for surgical breast procedures, including a pre-shaped tissue matrix, according to certain embodiments.

Also disclosed herein are methods for treating a breast by implanting the tissue product. Accordingly, FIG. 4 illustrates implantation of a system for surgical breast procedures, including a pre-shaped tissue matrix 32 implanted with a breast implant or tissue-expander, according to certain embodiments. The method can first include identifying an anatomic site within a breast 60. (As used herein, "within a breast" will be understood to be within mammary tissue, or within or near tissue surrounding the breast such as tissue just below, lateral or medial to the breast, or beneath surrounding tissues including, for example, under chest (pectoralis) muscles, and will also include implantation in a site in which part or all of the breast has already been removed via surgical procedure). The site can include, for example, any suitable site needing reconstruction, repair, augmentation, or treatment. Such sites may include sites in which surgical oncology procedures (mastectomy, lumpectomy) have been performed, sites where aesthetic procedures are performed (augmentation or revisions augmentation), or sites needing treatment due to disease or trauma.

Further provided herein are methods of treatment comprising the steps of selecting a tissue site and implanting the tissue products disclosed herein into the tissue site. The methods can include implanting the treatment device in or proximate to a wound or surgical site and securing at least a portion of the treatment device to tissue in or near the treatment site. The tissue product may be implanted behind the tissue site, in other words deep to the tissue site, to bolster, reposition, or project the native tissue outward.

Also provided herein are methods of treatment comprising selecting a tissue site within a breast; implanting a device within the tissue site; and allowing tissue to grow within the acellular adipose tissue matrix. In one embodiment, the device comprises a synthetic breast implant or tissue expander and an acellular adipose tissue matrix surrounding the breast implant or tissue expander. The method can further include removing the breast implant or tissue expander and implanting an additional acellular adipose tissue matrix within a void formed by removal of the breast implant or tissue expander.

The tissue products described herein can be used to treat a variety of different anatomic sites. For example, as discussed throughout, the tissue products of the present disclosure are produced from adipose tissue matrices and can be used for treatment of breasts. In some cases, the tissue products can be implanted in other sites, including, for example, tissue sites that are predominantly or significantly adipose tissue. In some cases, the tissue sites can include a breast (e.g., for augmentation, replacement of resected tissue, or placement around an implant). In addition, any other adipose-tissue containing site can be selected. For example, the tissue products may be used for reconstructive or cosmetic use in the breast, face, buttocks, abdomen, hips, thighs, or any other site where additional adipose tissue having structure and feel that approximates native adipose may be desired. In any of those sites, the tissue may be used to reduce or eliminate wrinkles, sagging, or undesired shapes.

Example: Effect of Cross-Linking on Adipogenesis 3D acellular adipose matrix (AAM) sponges reduce seroma, hematoma, and scar formation, as well as promote adipogenesis. The mechanical properties of the sponges must be able to properly withstand the compressive forces in the body. In order to improve the mechanical strength and resilience of 3D AAM sponges, the sponges were altered by chemical cross-linking (e.g., 1-Ethyl-3-(3-dimethylaminopropyl)carbodiimide; EDC). Yet there is often a tradeoff between biological response and mechanical strength achieved by cross-linking. Therefore, a subcutaneous nude rat model was used to assess the biological response to the cross-linked sponges.

AAM slurry was prepared, freeze dried, and by DHT cross-linked at 80° C. for 24 hours. The sponges were crosslinked in either 0.016% or 0.125% EDC. N-hydroxysuccinimide (NHS) was also added at a 5:3 EDC:NHS ratio. Sponges were then terminally sterilized by e-beam with 10 kGy for the uncross-linked sponges and 15 kGy for the cross-linked sponges. Sponges with a thickness of approximately 5 mm were cut with an 8 mm biopsy punch, washed in saline for 20-30 minutes, and then implanted subcutaneously into nude rats (n=4). At 4 weeks, the explants were cut in half, with one half fixed in 10% formalin for Masson's trichrome staining and the other half fixed in sucrose for Oil Red O staining.

Figure 5A:
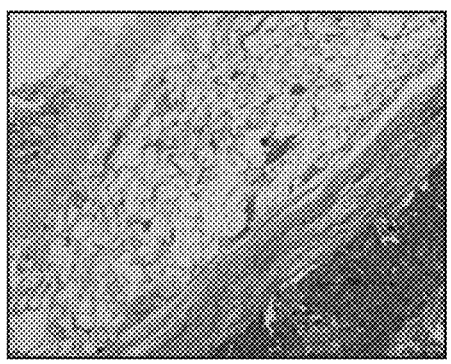
FIGS. 5A-5G are histologic images showing the effect of EDC crosslinking on adipogenesis.
Figure 5B:
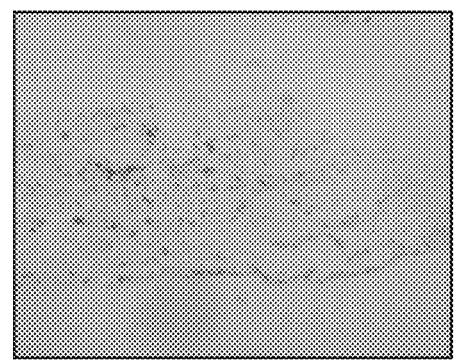
Figure 5C:
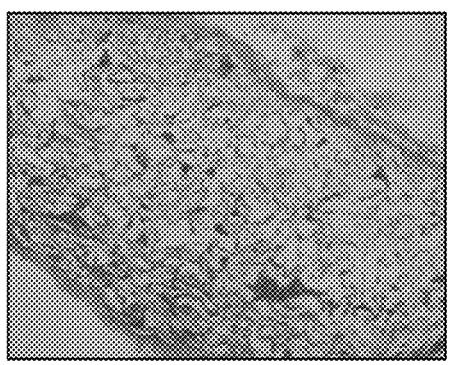
Figure 5D:
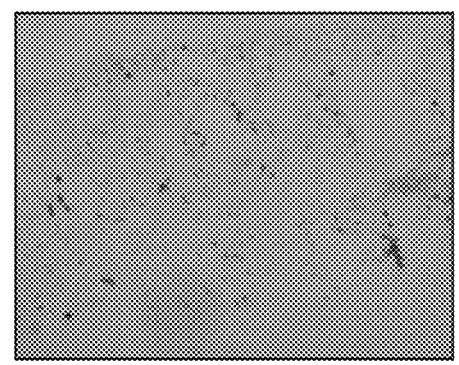
Figure 5E:
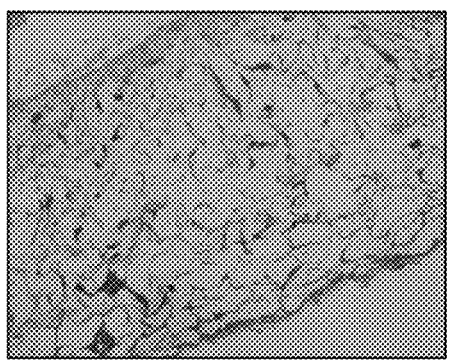
Figure 5F:
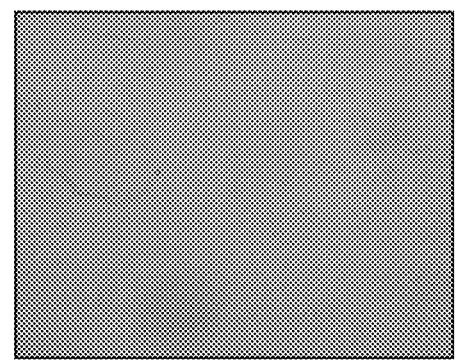
Figure 5G:
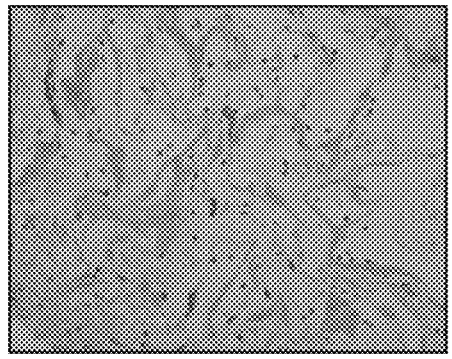

By 4 weeks the uncross-linked sponges exhibited cell ingrowth, vascularization, and adipogenesis (FIGS. 5A and B). In contrast, the 0.125% EDC cross-linked sponges did not exhibit any adipocytes by Oil Red O staining (FIGS. 5E and F). Sponges with an intermediate amount of cross-linking (0.016%) showed a level of adipocytes that was intermediate to the levels found in the 0.125% and uncross-linked sponges (FIGS. 5C and D). However, trichrome staining revealed extensive cell ingrowth and vascularization for all sponge types (FIGS. 5A, C, E, and G). This suggests that adipogenesis may be merely delayed by EDC cross-linking, not prevented entirely.

Overall, as EDC cross-linking was increased there was a concomitant decrease in adipogenesis, as evidenced by trichrome and Oil Red O staining. All three sponge types promoted cell ingrowth and vascularization regardless of the cross-linking conditions.

Example: Effect of Processing on Mechanical Properties

AAM must have mechanical properties to properly withstand the compressive forces in the body. In order to improve the mechanical strength and resilience of 3D AAM sponges, the sponges were altered by (1) changing the AAM solid content, (2) chemical cross-linking (e.g., 1-Ethyl-3-(3-dimethylaminopropyl)carbodiimide; EDC), and (3) adding tropoelastin. Incorporation of tropoelastin, a precursor of the extracellular matrix protein elastin, can change the mechanical properties (e.g., elasticity and resilience) of AAM.

AAM slurry was prepared with either a 3% or 4% solid content in 20% PBS. The slurry was then freeze dried to form sponges, followed by DHT cross-linking at 80° C. for 24 hours. The sponges were formed of slurry with 3 or 4% solid content, and if cross-linked with EDC were incubated at room temperature for 4 hours in either 0.03% or 0.1% EDC in MES buffer. N-hydroxysuccinimide (NHS) was also added to the buffer at a 5:3 EDC:NHS ratio. Following cross-linking, the sponge was washed twice with PBS. The sample solid content and EDC amount were as follows:

| Sample # | Sample Name |
|---|---|
| 1 | 3% AAM |
| 2 | 4% AAM |
| 3 | 3% AAM 0.03% EDC |
| 4 | 4% AAM 0.03% EDC |
| 5 | 3% AAM 0.1% EDC |
| 6 | 4% AAM 0.1% EDC |

In another sponge composition not shown here, 10 mg/ml tropoelastin in PBS was cross-linked with 10 mM bis(sulfosuccinimidyl)suberate (BS3) at 37° C. for 18 hours. The tropoelastin hydrogel was then cut and incorporated into the AAM slurry to a final concentration of 1%. The tropoelastin and AAM slurry was then freeze dried to form sponges and cross-linked as described above.

Compression testing was performed on sponges hydrated with PBS to assess compressive strength at 50% strain, percent shape recovery following compression, and modulus. Here, modulus is defined as the slope of the linear region of the force-displacement curve. Tensile testing was performed to assess elasticity with sponge strips that were hydrated with PBS and then gently squeezed to remove excess liquid.

Figure 6A:
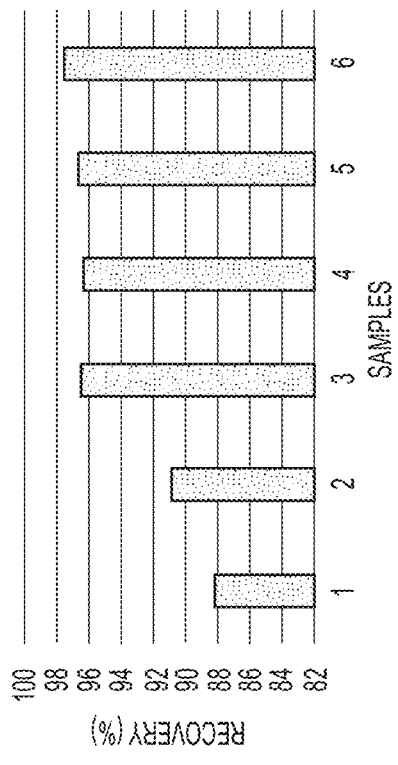
FIG. 6A is a bar graph showing the effect of adipose matrix solid content on compressive strength.
Figure 6B:
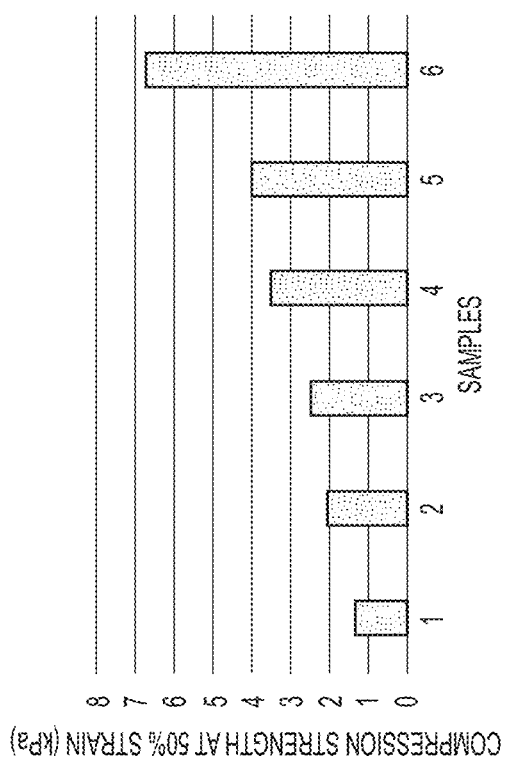
FIG. 6B is a bar graph showing the effect of adipose matrix solid content on recovery percentage.
Figure 6C:
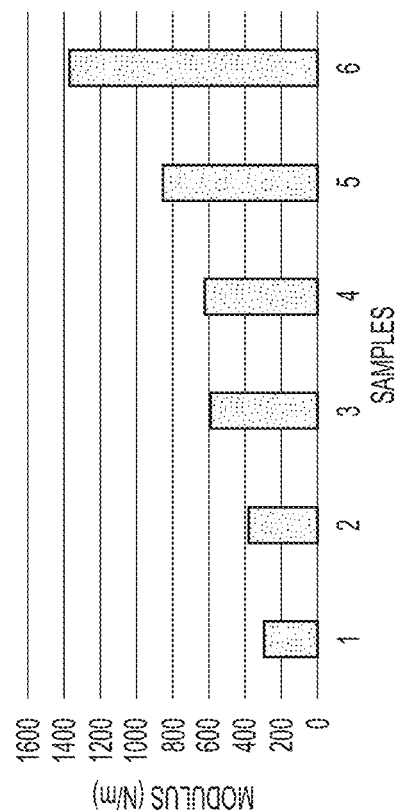
FIG. 6C is a bar graph showing the effect of adipose matrix solid content on elasticity.
Figure 6D:
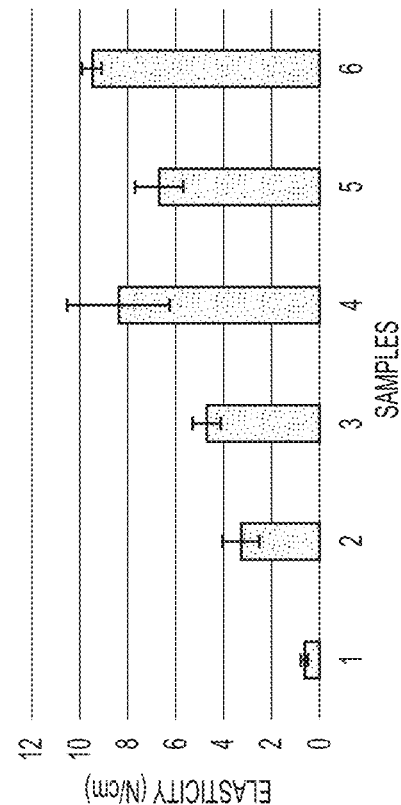
FIG. 6D is a bar graph showing the effect of adipose matrix solid content on modulus.

There was an overall linear trend for compressive strength, elasticity, and modulus as EDC percentage was increased (FIG. 6A, C, D). For each EDC cross-linking condition, the 4% AAM sponge was stronger than its 3% counterpart. The 4% AAM sponge with 0.1% EDC (Sample 6) exhibited the highest strength by these parameters. FIG. 6B shows that both the 0.03% and 0.1% EDC cross-linking conditions on average similarly improved shape recovery 7.2% over the uncross-linked versions.

Increasing the solid content from 3% to 4% improved mechanical strength of the sponges. EDC cross-linking the sponges further improved mechanical strength, with the higher EDC concentration (0.1%) resulting in stronger sponges than the lower EDC concentration (0.03%).

The invention claimed is:
1. A method for producing a tissue product, comprising the steps of:
    selecting an adipose tissue;
    treating the tissue to remove substantially all cellular material from the tissue;
    suspending the tissue in a liquid to form a suspension with a 2-4% by weight solid content; and
    freezing and drying the suspension to form a porous sponge.
2. The method of claim 1, further comprising cross-linking the porous sponge.
3. The method of claim 2, wherein cross-linking is performed using a dehydrothermal process.
4. The method of claim 3, further comprising performing a chemical cross-linking step.
5. The method of claim 1, wherein the porous sponge comprises a desired thickness at least in the thickest part of the sponge, the desired thickness exceeding 10.0 cm.
6. The method of claim 1, further comprising adding the suspension to a mold.
7. The method of claim 6, wherein the mold is in the shape of a round or a tear-drop breast implant.
8. The method of claim 4, wherein the chemical cross-linking step includes at least one of glutaraldehyde, genepin, carbodiimides, and diisocyanates.
9. The method of claim 4, wherein cross-linking includes heating the porous sponge.

10. The method of claim 9, wherein the porous sponge is heated in a vacuum.

11. The method of claim 10, wherein the porous sponge is heated to a range of 70° C. to 120° C.

12. The method of claim 4, wherein the porous sponge is cross-linked such that the material maintains a stable three-dimensional structure when contacted with an aqueous environment.

13. The method of claim 12, wherein the aqueous environment is a mammalian body.

14. A tissue product, comprising:
a breast implant, the implant comprising a construct of acellular adipose tissue matrix including particulate acellular adipose tissue matrix that has been formed into a suspension, dried, and stabilized, wherein the suspension comprises 2-4% by weight solid content, and wherein the implant measures at least 5 cm in at least one dimension.

15. The tissue product of claim 14, wherein the implant measures at least 8 cm in at least one dimension.

16. The tissue product of claim 14, wherein the implant is in the form of a rounded breast implant.

17. The tissue product of claim 14, wherein the implant is in the form of a tear-drop shaped breast implant.

18. The tissue product of claim 14, wherein the implant is produced by a process comprising:
selecting an adipose tissue;
treating the tissue to remove substantially all cellular material from the tissue;
suspending the tissue in a liquid to form a suspension with a 2-4% by weight solid content; and
freezing and drying the suspension to form a porous sponge.

19. The tissue product of claim 14, wherein the suspension is stabilized by cross-linking.

* * * * *